United States Patent [19]

Simpson

[11] Patent Number: 4,889,928

[45] Date of Patent: Dec. 26, 1989

[54] SUCROSE ALKYL 4,6-ORTHOACYLATES

[75] Inventor: Philip J. Simpson, Tadley, England

[73] Assignee: Tate & Lyle Public Limited Company, England

[21] Appl. No.: 322,695

[22] Filed: Mar. 13, 1989

Related U.S. Application Data

[63] Continuation-in-part of Ser. No. 97,194, Sep. 16, 1987, abandoned.

[30] Foreign Application Priority Data

Sep. 17, 1986 [GB] United Kingdom ................ 8622345

[51] Int. Cl.$^4$ .................... C07H 13/04; C07H 15/20; C07D 307/20; C07D 309/12
[52] U.S. Cl. .................................... 536/122; 536/115; 536/119; 536/124
[58] Field of Search ................ 536/115, 119, 124, 122

[56] References Cited

U.S. PATENT DOCUMENTS

| | | | |
|---|---|---|---|
| 4,362,869 | 12/1982 | Jenner et al. | 536/122 |
| 4,380,476 | 4/1983 | Mufti et al. | 536/122 |
| 4,405,654 | 9/1983 | Lee | 536/122 |

FOREIGN PATENT DOCUMENTS

| | | |
|---|---|---|
| 1543167 | 3/1979 | United Kingdom . |
| 2182039 | 5/1987 | United Kingdom . |

*Primary Examiner*—Ronald W. Griffin
*Attorney, Agent, or Firm*—Ostrolenk, Faber, Gerb & Soffen

[57] ABSTRACT

Sucrose 6-acylates, key intermediates in the preparation of sucralose, can be prepared by subjecting a sucrose alkyl 4,6-orthoacylate to mild aqueous acidic hydrolysis to provide a mixture of sucrose 4- and 6-acylates and then treating the mixture with a base to convert the 4-acylate to the 6-acylate.

The novel sucrose alkyl 4,6-orthoacylates are prepared by reacting sucrose in solution or suspension in an inert organic solvent with a trialkyl orthoacrylate in the presence of an acid catalyst.

16 Claims, No Drawings

SUCROSE ALKYL 4,6-ORTHOACYLATES

This is a continuation-in-part of application Ser. No. 097,194, filed Sept. 16, 1987, now abandoned.

This invention relates to novel sucrose derivatives, the cyclic 4,6-orthoesters of sucrose, and in particular to a process for the preparation of sucrose 6-esters using the 4,6-orthoesters as starting materials. Sucrose 6-esters are key intermediates in one process for the preparation on sucralose, a high intensity sweetener having a sweetness several hundred times that of sucrose (British Patent Specification No. 1543167).

The preparation of sucralose involves the introduction of chlorine atoms into the 1'- and 6'-positions (i.e. the displacement of two of the three primary hydroxy groups) and at the 4- position (i.e. the displacement of a secondary hydroxy group). The third primary hydroxy group, at the 6- position, must remain unaffected.

One important route to sucralose involves the preparation of 2,3,6,3',4'-penta-O-acetyl sucrose, in which the three hydroxy groups to be reacted are unprotected, while all the remaining hydroxy groups are protected. (See, for example, U.S. Pat. No. 4362869 or EP 31651B).

Selectively protecting the five positions not to be chlorinated, while exposing the three positions to be chlorinated, provides a number of technical difficulties. An alternative approach is to prepare a sucrose 6-ester which can, under appropriate conditions, be selectively chlorinated in the 4, 1' and 6' positions. A method of preparing sucrose 6 esters, and their conversion into sucralose is disclosed in U.K. 2079749B. However, this process produces a mixture of acylated sucrose derivatives with substituents at one or more of the primary positions, but with the major proportion of 6-monoacylated sucrose. This is an attractive route to sucralose, but there is a need for a more selective method of producing sucrose 6-esters.

The present invention is based on the discovery that a novel range of sucrose derivatives can be readily obtained and that these derivatives, the 4,6-orthoesters, can be hydrolysed to give a mixture of sucrose 4- and 6-esters which can be simply isomerized to provide a high yield of 6-ester and the virtual absence of 4-ester.

Cyclic orthoesters of carbohydrates have been reported. The best known of these are bicyclic 1,2-glycopyranosyl derivatives which may be prepared from glycosyl halides and have been used as intermediates in the synthesis of disaccharides (Kochetkov & Bochkov in Methods in Carbohydrate Chemistry, VI, Academic Press New York and London 1972 p 480). Orthoesters at other positions are less well known, but Ferrier and Collins (in Monosaccharide Chemistry, Penguin Books, Harmondsworth, Middlesex 1972 p 196) mentioned that they may be prepared by the acid catalysed reactions of suitable carbohydrate diols and trialkyl orthoesters. It has now been found that the reaction of trialkyl orthoesters under acid catalysis with sucrose itself surprisingly gives a 4,6-orthoester in the absence of other isomers and in good yield. These 4,6-orthoesters of sucrose are novel compounds.

The novel sucrose derivatives of use in the present invention are sucrose alkyl 4,6-orthoacylates, namely compounds of the general formula

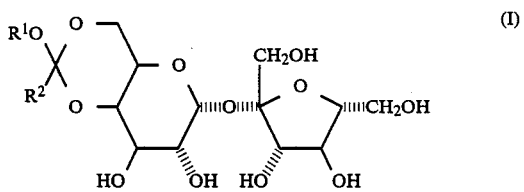

where $R^1$ represents an alkyl group, especially an alkyl group with 1–3 carbon atoms e.g. a methyl, ethyl or propyl group; and $R^2$ represents an alkyl or aryl group, preferably an alkyl group with 1–4 carbon atoms, e.g. a methyl, ethyl, propyl or butyl group, or a phenyl group. Particularly useful compounds of the general formula I include sucrose methyl 4,6-orthoacetate, sucrose ethyl 4,6-orthoacetate, sucrose methyl 4,6-orthobutyrate and sucrose methyl 4,6-orthobenzoate. These novel compounds represent one feature of the present invention.

According to the present invention there is provided a process for the preparation of a sucrose 6-acylate comprising subjecting a sucrose alkyl 4,6-orthoacylate to mild aqueous acidic hydrolysis to provide a mixture of 4- and 6-monoesters of sucrose and then treating the ester mixture with a base to convert the sucrose 4-ester into sucrose 6-ester.

In particular, there is provided a process for the preparation of a sucrose ester of the general formula II

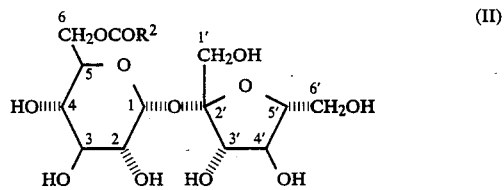

in which $R^2$ represents an alkyl or aryl group, by treatment of an orthoester of the general formula I

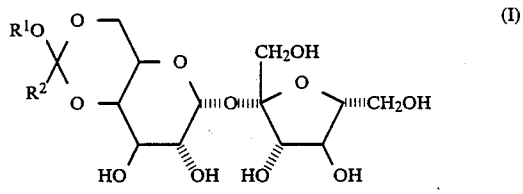

in which $R^1$ represents an alkyl group and $R^2$ is as defined for formula II, under mild aqueous acidic conditions followed by treatment with a base.

The initial mildly acidic treatment can be effected in aqueous solution in the presence of a catalytic amount of an acid such as toluene p-sulphonic acid or hydrochloric acid. However, for preference, the reaction is carried out in solution in an inert polar organic solvent such as dmf or pyridine containing some water and an acid such as those mentioned above, or pyridine hydrochloride. The amount of water added should be an excess over that required theoretically, typically 3 to 10 molar equivalents based on the sucrose ester, e.g. 4 to 8 ME. The acid should be sufficient to give a pH of about 5 to 6. The reaction proceeds effectively at ambient temperature. The reaction with a base, to isomerise the 4-ester to the 6-ester, can conveniently be effected in the same solution, simply by adding sufficient base to neutralize the acid and to provide a small excess. Typical bases of use include tertiary amines such as pyridine and its analogues, tertiary alkylamines such as t-butylamines, and alkaline earth metal hydroxides such as calcium hydroxide. Again, the reaction proceeds at ambient temperature.

An exception to the above is the case of the orthobenzoate, where cleavage requires more forcing conditions (i.e. a lower pH and a temperature above ambient).

The method of the present invention provides an easy and selective route to sucrose 6- esters and, since these can be easily chlorinated, it also provides a simple direct route to sucralose itself. Thus, according to a further feature of the present invention there is provided a process for the preparation of sucralose comprising reacting sucrose to prepare a sucrose 6-ester, reacting the sucrose 6-ester with a chlorinating agent capable of effecting selective clorination at the 4-,1' and 6'- positions, optionally peresterifying the sucralose 6-ester so formed and deesterifying the sucralose ester before or after the separation from the reaction mixture, and recovering sucralose, characterised in that the formation of the sucrose 6-ester is effected by cleaving a sucrose alkyl 4,6-orthoacylate under mildly acidic aqueous conditions followed by treatment with a base.

The chlorination step can be effected using any of the suitable chlorinating systems, for example those disclosed in GB No. 2 079 749B, for example a reagent of the Vilsmeier type, i.e. an N,N-dialkyl-(chloromethaniminium) chloride; a triarylphosphine or triarylphosphite; or sulphuryl chloride. Another useful chlorinating system is thionyl chloride in the presence of triphenyl phosphine oxide (see GB No. 2 182 039A).

The sucrose 4,6-orthoesters used as starting materials can be prepared selectively by the direct reaction of sucrose with a trialkyl orthoester in a suitable inert organic solvent such as dimethyl formamide or pyridine, in the presence of an acid catalyst. The reaction is virtually complete within one hour at ambient temperature with only traces of sucrose and an intermediate component present. After neutralising (e.g. with a suitable ion exchange resin) and filtering, the product can be recovered as a clear colourless syrup by evaporation of the filtrate under vacuum. The relatively mild reaction conditions are not conducive to the formation of unwanted by-products.

According to the present invention there is further provided a method for the preparation of sucrose 4,6-orthoesters by the reaction of sucrose with a trialkyl orthoester in the presence of an acid catalyst in an inert organic solvent or suspending agent.

The catalyst can be any strong acid and we have found it convenient to use p-toluene sulphonic acid, pyridinium chloride or tosylate or toluene sulphonic acid.

The following Examples illustrate the invention.

EXAMPLE 1

Preparation of sucrose methyl 4,6-orthoacetate

To a solution of sucrose (3.42 g) in dimethylformamide (27.5 ml) was added trimethyl orthoacetate (1.91 ml; 1.5 ME) and a catalytic amount of p-toluene sulphonic acid (25 mg). After one hour at ambient temperature, tlc (n-BuOH/EtOH/H$_2$O, 5:3:2) showed virtually complete reaction to a new compound (Rf 0.62) with only traces of sucrose (Rf 0.40) and an intermediate component (Rf 0.54) present. The solution was then neutralised using Amberlite IRA93(OH$^-$) ion exchange resin, filtered and the filtrate evaporated in vacuo to a clear colourless syrup (4.0 g). A sample of this material was acetylated by the conventional method using acetic anhydride in pyridine. The $^1$H NMR spectrum of the acetate was consistent with the structure. The mass spectrum of the hexaacetate was also consistent with the structure, giving M+ —OCH$_3$=619.

EXAMPLE 2

Preparation of sucrose 6-acetate

Sucrose methyl 4,6-orthoacetate (1 g) was dissolved in water (10 ml), solution pH 5. After one hour at ambient temperature tlc (n-BuOH/EtOH/H$_2$O, 5:3:2) showed a major component at Rf 0.54 with only a trace of the orthoacetate (Rf 0.62) and a little sucrose (Rf 0.40) remaining. HPLC analysis of the solution after two hours showed, inter alia, major components with retention times of 3.46 (sucrose), 4.66 (sucrose 4-acetate) and 8.63 (sucrose 6-acetate) in the approximate ratios 7:49:43. Pyridine (1 ml) was then added to the aqueous solution. Periodical HPLC analysis showed an increase in sucrose 6-acetate concentration with time and a decrease in sucrose 4-acetate. After 4 hours the ratios of sucrose: sucrose 4-acetate: sucrose 6-acetate were 11:3:85. The solution was then concentrated to dryness and the residue was dissolved in pyridine and evaporated in vacuo to a syrup to remove residual water. A solution of the syrup in pyridine (10 ml) was stored overnight over molecular sieve (4 A) in preparation for chlorination as described in Example 3.

EXAMPLE 3

Preparation of sucralose

Thionyl chloride (1.52 ml, 8 ME) was added to a solution of triphenylphosphine oxide (2.17 g, 3 ME) in pyridine (8 ml). The solution was heated to 50° before adding the solution of sucrose 6-acetate in pyridine (about 1 g in 10 ml) from Example 2. The mixture was heated to 95° and held at this temperature for one hour. The mixture was then acetylated in the conventional manner, using acetic anhydride in pyridine. Tlc (diethyl ether/petrol 4:1) of the acetylated reaction mixture showed a major component corresponding to sucralose pentaacetate, a trace of tetrachloro galactosucrose tetraacetate and base line material. The sucralose pentaacetate was separated by crystallisation, taken up in methanol and deacetylated by treatment with sodium methoxide in the conventional manner to yield sucralose (about 0.5 g).

EXAMPLE 4

Preparation of sucrose methyl 4,6-orthobutyrate (characterised as the hexaacetate)

A suspension of sucrose (10 g) in pyridine (50 ml) was treated with trimethyl orthobutyrate (5.2 ml: 1.1 ME) and pyridinium tosylate (500 mg) at 75° for 2.5 hours. The resulting solution was cooled to 30° and acetic anhydride (35 ml) was added, allowing the temperature to rise to 60°. After 1 hour at 60°, the solution was cooled to room temperature and methanol (20 ml) was added. The solution was then concentrated to dryness, dissolved in ethyl acetate (50 ml), and evaporated onto silica gel (Merck 7734).

Column chromatography, eluting with diethyl ether-petroleum ether 40°–60° (2:1) gave the pure sucrose methyl 4,6, orthobutyrate hexaacetate (16.2 g, 82%)

which was recrystallised from diethyl ether-petroleum ether (40°–60°) mp 84°–85°; $[\alpha]_D +55.2°$ (c 2.0, CHCl$_3$).

| $^1$H NMR (CDCl$_3$) | | | | | | |
|---|---|---|---|---|---|---|
| δ ppm | | | | | Hz | |
| 5.66 | d | 1H | H-1 | $J_{1,2}$ | 3.9 | |
| 5.44 | d | 1H | H-3' | $J_{3',4'}$ | 5.7 | |
| 5.38 | dd | 1H | H-4' | $J_{3',4'}$ | 5.7/$J_{4',5'}$ | 5.7 |
| 5.37 | dd | 1H | H-3 | $J_{2,3}$ | 10.0/$J_{3,4}$ | 9.9 |
| 4.82 | dd | 1H | H-2 | $J_{1,2}$ | 3.9/$J_{2,3}$ | 10.0 |
| 3.89 | dd | 1H | H-4 | $J_{3,4}$ | 9.9/$J_{4,5}$ | 9.7 |
| 3.83–4.33 multiplets 8H H-5, H-6(X2), H-1'(X2), H-5', H-6'(X2) | | | | | | |
| 3.26 | s | 3H | —OCH$_3$ | | | |
| 2.19 | s | 3H | —OAc | | | |
| 2.12 | s | 3H | —OAc | | | |
| 2.11 | s | 3H | —OAc | | | |
| 2.10 | s | 3H | —OAc | | | |
| 2.08 | s | 3H | —OAc | | | |
| 2.06 | s | 3H | —OAc | | | |
| 1.70 | m | 2H | —C$\underline{H_2}$CH$_2$CH$_3$ | | | |
| 1.40 | m | 2H | —CH$_2$C$\underline{H_2}$CH$_3$ | | | |
| 0.89 | t | 3H | —CH$_2$CH$_2$C$\underline{H_3}$ | | | |

EI mass spectrum MW 678
m/e  679 MH$^+$
     647 MH$^+$—MeOH
     331 F$^+$OAc$_4$ & OBuG$^+$OAc$_2$ By an analogous method, using the corresponding trialkyl orthoesters, the following compounds were prepared:

| Sucrose methyl 4,6-orthoacetate hexaacetate [4,6-O—(1-methoxyethylidene)-sucrose hexaacetate] | | | | | | |
|---|---|---|---|---|---|---|
| cryst. diethyl ether/petroleum ether 40–60° mp 79–81° $[\alpha]_D + 61.0°$ (c 2.0, CHCl$_3$) | | | | | | |
| δ ppm | | | | | Hz | |
| 5.66 | d | 1H | H-1 | $J_{1,2}$ | 3.9 | |
| 5.44 | d | 1H | H-3' | $J_{3',4'}$ | 5.5 | |
| 5.39 | dd | 1H | H-3 | $J_{2,3}$ | 9.8 / $J_{3,4}$ 9.8 | |
| 5.37 | dd | 1H | H-4' | $J_{3',4'}$ | 5.5 / $J_{4',5'}$ 5.5 | |
| 4.81 | dd | 1H | H-2 | $J_{2,3}$ | 9.8 / $J_{1,2}$ 3.9 | |
| 4.30–3.84 | m | 9H | H-4, H-5, H-6(X2), H-1' (X2), H-5', H-6(X2) | | | |
| 3.29 | s | 3H | —OMe | | | |
| 2.20 | s | 3H | —OAc | | | |
| 2.12 | s | 3H | —OAc | | | |
| 2.11 | s | 3H | —OAc | | | |
| 2.10 | s | 3H | —OAc | | | |
| 2.08 | s | 3H | —OAc | | | |
| 2.07 | s | 3H | —OAc | | | |
| 1.45 | s | 3H | —Me | | | |

EI mass spectrum   MW 650
m/e 651 MH$^+$
    619 MH$^+$—MeOH
    331 F$^+$OAc$_4$
    303 OAcG$^+$OAc$_2$

| Sucrose ethyl 4,6-orthoacetate hexaacetate [4,6-O—(1-ethoxyethylidene)-sucrose hexaacetate] | | | | | | |
|---|---|---|---|---|---|---|
| cryst.diethyl ether - petroleum ether 40–60° mp 93–95° $[\alpha]_D + 59.2°$ (c 2.0, CHCl$_3$) | | | | | | |
| $^1$H NMR (CDCl$_3$) | | | | | | |
| δ ppm | | | | | Hz | |
| 5.64 | d | 1H | H-1 | $J_{1,2}$ | 3.8 | |
| 5.43 | d | 1H | H-3' | $J_{3',4'}$ | 5.6 | |
| 5.38 | dd | 1H | H-3 | $J_{2,3}$ | 9.9/$J_{3,4}$ | 10.2 |
| 5.36 | dd | 1H | H-4' | $J_{3',4'}$ | 5.6/$J_{4',5'}$ | 5.6 |

| Sucrose ethyl 4,6-orthoacetate hexaacetate [4,6-O—(1-ethoxyethylidene)-sucrose hexaacetate] | | | | | | |
|---|---|---|---|---|---|---|
| cryst.diethyl ether - petroleum ether 40–60° mp 93–95° $[\alpha]_D + 59.2°$ (c 2.0, CHCl$_3$) | | | | | | |
| $^1$H NMR (CDCl$_3$) | | | | | | |
| δ ppm | | | | | Hz | |
| 4.82 | dd | 1H | H-2 | $J_{2,3}$ | 9.9/$J_{1,2}$ | 3.8 |
| 4.33–3.85 | m | 9H | H-4, H-5, H-6(X2), H-1'(X2), H-5', H-6'(X2) | | | |
| 3.51 | s | 2H | —OC$\underline{H_2}$CH$_3$ | | | |
| 2.20 | s | 3H | —OAc | | | |
| 2.12 | s | 3H | —OAc | | | |
| 2.11 | s | 3H | —OAc | | | |
| 2.10 | s | 3H | —OAc | | | |
| 2.08 | s | 3H | —OAc | | | |
| 2.07 | s | 3H | —OAc | | | |
| 1.46 | s | 3H | —CH$_3$ | | | |
| 1.26 | t | 3H | —OCH$_2$C$\underline{H_3}$ $J_7$, | | | |

EI mass spectrum MW 664
m/e  665 MH$^+$
     619 MH$^+$—EtOH
     331 F$^+$OAc$_4$
     317 OAcG$^+$OAc$_2$

| Sucrose methyl 4,6-orthobenzoate hexaacetate | | | | | | |
|---|---|---|---|---|---|---|
| Syrup $[\alpha]_D + 40.8°$ (c 2.0, CHCl$_3$) | | | | | | |
| $^1$H NMR (CDCl$_3$) | | | | | | |
| δ ppm | | | | | Hz | |
| 7.52–7.28 | m | 5H | Ph | | | |
| 5.71 | d | 1H | H-1 | $J_{1,2}$ | 3.9 | |
| 5.51 | dd | 1H | H-3 | $J_{2,3}$ | 10.0 / $J_{3,4}$ 9.8 | |
| 5.44 | d | 1H | H-3' | $J_{3',4'}$ | 5.6 | |
| 5.37 | dd | 1H | H-4' | $J_{3',4'}$ | 5.6/$J_{4',5'}$ 5.7 | |
| 4.91 | dd | 1H | H-2 | $J_{1,2}$ | 3.9/$J_{2,3}$ 10.0 | |
| 4.08 | dd | 1H | H-4 | $J_{3,4}$ | 9.8/$J_{4,5}$ 9.4 | |
| 4.04–4.30 | m | 8H | H-5, H-6(X2), H-1' (X2), H-5', H-6' (X2) | | | |
| 3.06 | s | 3H | —OCH$_3$ | | | |
| 2.17 | s | 3H | —OAc | | | |
| 2.12 | s | 3H | —OAc | | | |
| 2.11 | s | 3H | —OAc | | | |
| 2.10 | s | 3H | —OAc | | | |
| 2.09 | s | 3H | —OAc | | | |
| 2.02 | s | 3H | —OAc | | | |

EI mass spectrum    MW 712
m/e 681 MH$^+$—MeOH
    365 oBzG$^+$OAC$_2$
    331 F$^+$OAc$_4$

EXAMPLE 5

Cleavage of orthoesters

The procedure of Example 1 was carried out. Then, instead of the procedure of Example 2, the following method was used for the cleavage step:

Once orthoester formation was complete, addition of 10% by volume of water (8 ME based on sucrose) to the DMF solution, without neutralisation of the p-toluene sulphonic acid, gave a pH of 5.5. Cleavage of the orthoester occurred cleanly under these conditions but required at least 1 hour, allowing a noticeable amount of sucrose to be regenerated. By increasing the concentration of acid from the original 4 up to 6 mg/g sucrose, the cleavage time was reduced to approximately 20 minutes and considerably less sucrose was regenerated (see Table 1). When the added water was halved to 5%

(4 ME), cleavage was almost as rapid but acetate migration was slower.

TABLE 1
Effect of acid and water concentration on the rate of orthoester cleavage in DMF solution

| TsOH used (mg/g sucrose) | water added (ME) | time within which cleavage was completed (min) |
|---|---|---|
| 4 | 8 | 70 |
| 6 | 8 | 20 |
| 6 | 4 | 25 |

EXAMPLE 6

Acetate migration in DMF

In a modification of the method of Example 2, t-butylamine was used instead of pyridine to effect the acetate migration. Addition of 2.5% by volume to the wet DMF solution raised the pH to approximately 9. Under these conditions, acetate migration was complete within 1 hour, when HPLC indicated 87% sucrose 6-acetate, 3% sucrose 4-acetate and 10% sucrose to be present. (See Table 2). Reduction of the t-butylamine to 1.25%, or of the water to 5%, slowed the migration considerably, allowing a build up in the sucrose concentration. When migration was complete, the solution was concentrated under vacuum to a viscous syrup from which most of the DMF was removed by co-evaporation with toluene.

TABLE 2
Effect of t-butylamine and water concentration on the rate of acetate migration

| t-BuNH$_2$ % by vol | H$_2$O % by vol | Time after addition of t-BuNH$_2$ (min) | Carbohydrate Composition % by HPLC | | |
|---|---|---|---|---|---|
| | | | S4A | S6A | S |
| | | 0 | 31.6 | 56.4 | 12.0 |
| | | 30 | 25.0 | 62.8 | 12.2 |
| 1.25 | 5 | 120 | 10.1 | 76.8 | 13.0 |
| | | 180 | 6.4 | 80.2 | 13.3 |
| | | | 31.3 | 56.9 | 11.8 |
| | | 30 | 18.5 | 67.5 | 14.0 |
| 2.5 | 5 | 60 | 9.2 | 75.3 | 15.5 |
| | | 135 | 3.2 | 80.6 | 16.1 |
| | | 0 | 37.5 | 52.5 | 9.9 |
| 2.5 | 10 | 30 | 13.4 | 76.2 | 10.4 |
| | | 60 | 2.1 | 86.9 | 11.0 |

S = sucrose, S4A = sucrose 4-acetate, S6A = sucrose 6-acetate

EXAMPLE 7

Preparation of Sucrose 6-acetate

The procedure of Examples 5 and 6 were combined as follows:

A stirred suspension of sucrose (50 g) in DMF (200 ml) was treated with trimethyl orthoacetate (21 ml: 1.1 ME) and p-toluene sulphonic acid (300 mg) at 20° C. After 2.5 hours, water (20 ml: 8 ME) was added to the clear solution. After a further 20 min., t-butylamine (5 ml) was added. Stirring was continued for a further 1 hour before the mixture was concentrated under vacuum. DMF was removed by repeated co-evaporation with toluene (2×200 ml, approximately) to leave crude sucrose 6-acetate as a thick colourless syrup.

Yield approximately 83 g (still containing 25% DMF).

Approximate carbohydrate composition: sucrose 6-acetate; 87%, sucrose 4-acetate; 3%, sucrose; 10%.

The whole sequence was monitored by HPLC using a Zorbax NH$_2$ column, eluting with aqueous acetonitrile (85% v/v) at 1.5 ml/min and using 2 μl injections of neat reaction mixture.

EXAMPLE 8

Preparation of 100 g batches of sucrose 6-acetate in DMF

Five (100 g) batches of sucrose 6-acetate were produced using the following method of preparation.

Sucrose (100 g; icing sugar dried in vacuum oven for 24 hours at 60° C.), trimethyl orthoacetate (48 ml, 1.25 ME) and p-toluene sulphonic acid (600 mg) were suspended in DMF (400 ml) and the mixture was stirred at room temperature (20°–22° C.) for 3 hours. The progress of the reaction was monitored by HPLC. The reaction mixture became clear after 1.25 hours. At that point the first sample for HPLC was taken out. The first stage of the reaction was considered complete when consecutive traces were found to be indistinguishable.

At this stage water (40 ml, 8 ME) was added to the reaction mixture at room temperature to cleave the 4,6-orthoacetate ring. According to HPLC the cleavage of orthoacetate ring to a mixture of sucrose 4- and 6-acetates was complete in approximately 1 hour.

In order to migrate the 4-acetate to the 6-position, tert-butylamine (10 ml) was added and the reaction mixture stirred at ambient temperature for 1.25 hours. When HPLC indicated that no further migration was taking place the reaction mixture was concentrated to a syrup under reduced pressure at 80°–85° C.

| Average analysis of product | |
|---|---|
| weight | 154 g |
| carbohydrate composition by HPLC | |
| sucrose 6-acetate | 84% |
| sucrose 4-acetate | 4% |
| sucrose | 12% |
| residual solvents | |
| DMF | 24% |
| methanol | 0.1% |
| toluene | 1.0% |
| water | 1.5% |

The product could be used for chlorination to produce sucralose as in Example 3 above.

A sample of sucrose 6-acetate was purified by crystallisation from methanol to give mp 94°–96°; ]α]$_D$+60.3° (c 2.0, H$_2$O)

| $^{13}$C NMR (DMSO-d$_6$) ppm | | |
|---|---|---|
| Sucrose 6-acetate | | Sucrose |
| 170.5 | —CO—CH$_3$ | |
| 103.9 | 2' | 104.4 |
| 91.5 | 1' | 92.4 |
| 82.8 | 5' | 82.8 |
| 77.0 | 3' | 77.4 |
| 74.6 | 4' | 74.7 |
| 72.8 | 3 | 73.3 |
| 71.6 | 2 | 72.0 |
| 70.3* | 5 | 73.3* |
| 70.0 | 4 | 70.2 |
| 63.9* | 6 | 60.9* |
| 62.7 | 6' | 62.6 |
| 62.3 | 1' | 62.4 |
| 20.8 | —CO—CH$_3$ | |

*significant difference

EXAMPLE 9

Preparation of sucrose 6-acetate for conversion to sucralose

To a stirred suspension of sucrose (1.5 Kg) in dimethylformamide (3000 ml) at 60° C. was added trimethylorthoacetate (863 ml) and concentrated sulphuric acid (3 ml). After heating for about two hours the mixture was cooled to 25° C. and concentrated sulphuric acid (0.3 ml) in water (470 ml) was added. The temperature rose to about 40° C. and cooling was maintained to return the temperature to 25° C. After 30 minutes calcium hydroxide (6 g) was added and migration of acetate from the 4- to the 6- position was allowed to proceed for one hour. The reaction was then quenched with a 1:10 concentrated sulphuric acid:water mixture (21 ml). The insoluble material (calcium sulphate) was removed by filtration and the filtrate was concentrated to a syrup (2.48 IKg) under reduced pressure at 80°–85° C. The syrup was dissolved in hot methanol (3000 ml), the solution was seeded with sucrose 6-acetate (7.5 g) and crystallization was allowed to proceed for about four hours. The product was collected, washed with methanol (6×250 ml) and dried under vacuum at 45° C. Yield 990 g (48%) comprising about 80% sucrose 6-acetate.

The product was chlorinated sucralose as described in Example 3.

I claim:

1. A process for the preparation of a sucrose 6-acylate which comprises subjecting a sucrose alkyl 4,6-orthoacylate to mild aqueous acidic hydrolysis to provide a mixture of 4- and 6- monoesters of sucrose and then treating the ester mixture with a base to convert the sucrose 4-ester into sucrose 6- ester.

2. The process of claim 1 for the preparation of a sucrose ester of the general formula II

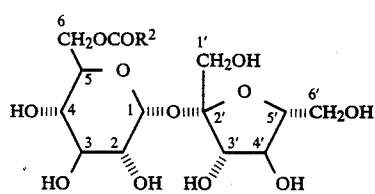

(II)

in which $R^2$ represents $C_{1-4}$ alkyl or phenyl group, by treatment of an orthoester of the general formula I

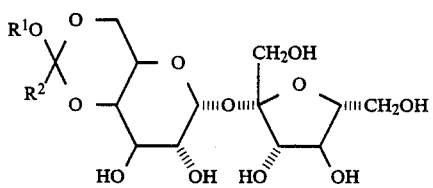

(I)

in which $R^1$ represents $C_{1-3}$ alkyl group and $R^2$ is as defined for formula II, under mild aqueous acidic conditions followed by treatment with a base.

3. The process of claim 1 in which the mild aqueous acidic treatment is effected in an inert polar organic solvent containing water in an excess of one molar equivalent.

4. The process claim 1, in which the base treatment is effected using a tertiary amine.

5. The process of claim 4 in which the base treatment is effected in the same solution used for the acid treatment.

6. Process of claim 1 in which a sucrose ester of the general formula II

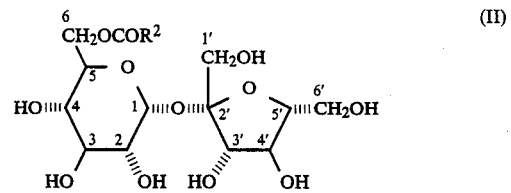

(II)

in which $R^2$ represents $C_{1-4}$ alkyl or aryl, is treated with an orthoester of the general formula I

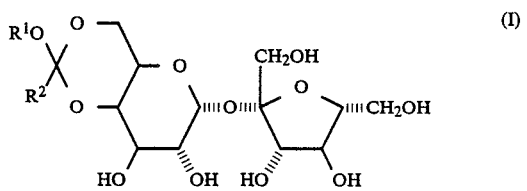

(I)

in which $R^1$ represents $C_{1-3}$ alkyl group and $R^2$ is as defined for formula II, under mild aqueous acidic conditions followed by treatment with a base.

7. The process of claim 1 in which the mild aqueous acidic treatment is effected in an inert polar organic solvent containing water in an excess of one molar equivalent.

8. The process claim 1, in which the base treatment is effected using a tertiary amine.

9. A sucrose alkyl 4,6-orthoacylate.

10. A compound according to claim 9 of the formula:

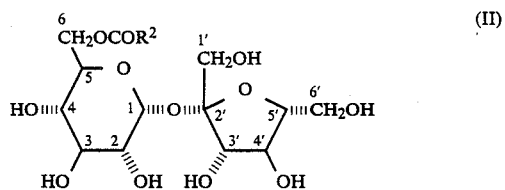

(II)

where $R^1$ represents $C_{1-3}$ alkyl, and $R^2$ represents $C_{1-4}$ alkyl or phenyl.

11. The compound of claim 10 selected from the group consisting of sucrose methyl 4,6-orthoacetate, sucrose ethyl 4,6-orthoacetate, sucrose methyl 4,6-orthobutyrate and sucrose methyl 4,6orthobenzoate.

12. A method of preparing a sucrose alkyl 4,6-orthoacylate comprising reacting sucrose in solution or suspension in an inert organic solvent with a trialkyl orthoacylate in the presence of an acid catalyst.

13. The process of claim 3 in which the solvent contains 3 to 10 molar equivalents of water.

14. In a process for the preparation of sucralose comprising the steps of preparing a sucrose 6-ester, reacting the sucrose 6-ester with a chlorinating agent to effect chlorination at the 4, 1' and 6' positions, separating the sucralose ester and recovering sucralose, the improvement which comprises preparing the sucrose 6-ester by subjecting a sucrose alkyl 4,6-orthoacylate to mild aqueous acidic hydrolysis to obtain a mixture of monoesters of sucrose and treating the mixture of monoesters so-formed with a base to convert the sucrose 4-ester into sucrose 6-ester.

15. The process of claim 7 in which the solvent contains 3 to 10 molar equivalents of water.

16. The process of claim 3 in which the mild aqueous acidic treatment is effected in dimethylformamide or pyridine containing 4 to 8 molar equivalents of water and toluene p-sulphonic acid or hydrochloric acid having a pH of about 5 to 6.

* * * * *

UNITED STATES PATENT AND TRADEMARK OFFICE
CERTIFICATE OF CORRECTION

PATENT NO. : 4,889,928

DATED : December 26, 1989

INVENTOR(S) : Philip J. Simpson

It is certified that error appears in the above-identified patent and that said Letters Patent is hereby corrected as shown below:

Abstract, penultimate line, for "orthoacrylate" read --orthoacylate--.

Column 8, line 49, for "]$\alpha$]$_D$" read --[$\alpha$]$_D$--.

Column 9, line 28, after "chlorinated" read --to produce--.

Column 10, line 4, for "1" read --14--; line 15, for "treated with" read --prepared by treatment of--; line 30, for "1" read --14--; and line 34, for "1" read --14--.

Signed and Sealed this

Thirty-first Day of March, 1992

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,889,928  
APPLICATION NO. : 07/322695  
DATED : December 26, 1989  
INVENTOR(S) : Philip J. Simpson Page 1 of 1

It is certified that error appears in the above-identified patent and that said Letters Patent is hereby corrected as shown below:

On Title page item 57
  Abstract, penultimate line, for "orthoacrylate" read --orthoacylate--.

Column 8, line 49, for "]$\alpha]_D$" read --$[\alpha]_D$--.

Column 9, line 28, after "chlorinated" read --to produce--.

Column 10, line 4, for "1" read --14--; line 15, for "treated with" read --prepared by treatment of--; line 30, for "1" read --14--; and line 34, for "1" read --14--.

Signed and Sealed this

Thirtieth Day of January, 2007

JON W. DUDAS  
*Director of the United States Patent and Trademark Office*

UNITED STATES PATENT AND TRADEMARK OFFICE
CERTIFICATE OF CORRECTION

PATENT NO. : 4,889,928
APPLICATION NO. : 07/322695
DATED : December 26, 1989
INVENTOR(S) : Simpson It is certified that error appears in the above-identified patent and that said Letters Patent is hereby corrected as shown below:

In the Claims

Column 9, line 67, "process claim 1" should read --process of claim 1--.

Column 10, line 34, "process claim 1" should read --process of claim 1--.

Column 10, lines 38-48, the chemical structure

" 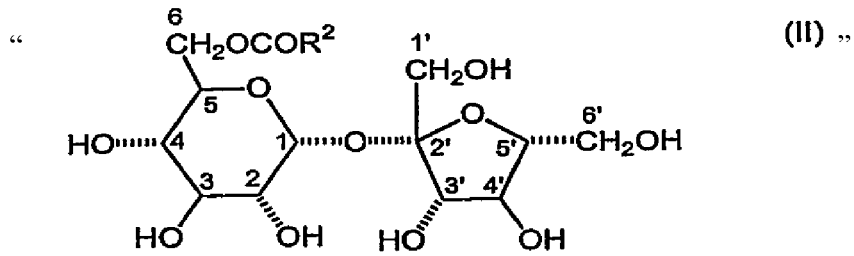 (II) "

should read

-- 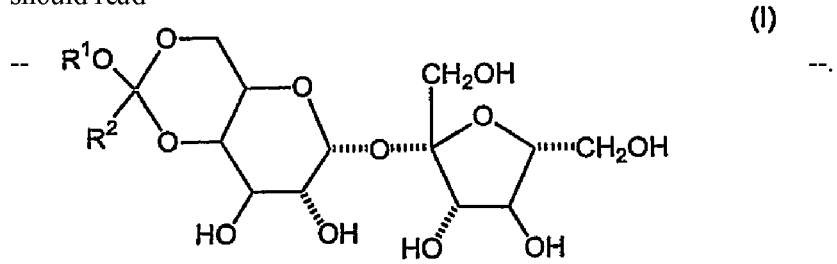 (I) --.

Col. 10, line 54, "4,6orthobenzoate" should read --4,6-orthobenzoate--.

Signed and Sealed this

Seventeenth Day of April, 2007

JON W. DUDAS
*Director of the United States Patent and Trademark Office*